(12) United States Patent
Yogesan et al.

(10) Patent No.: US 7,083,281 B2
(45) Date of Patent: Aug. 1, 2006

(54) PORTABLE SLIT LAMP

(75) Inventors: Kanagasingam Yogesan, Nedlands (AU); Ian Jeffrey Constable, Mosman Park (AU); Gabriel Suplewski, Currambine (AU)

(73) Assignee: The Lions Eye Institute of Western Australia, Inc., Western Australia (AU)

( * ) Notice: Subject to any disclaimer, the term of this patent is extended or adjusted under 35 U.S.C. 154(b) by 101 days.

(21) Appl. No.: 10/296,020

(22) PCT Filed: May 18, 2001

(86) PCT No.: PCT/AU01/00570

§ 371 (c)(1),
(2), (4) Date: Nov. 15, 2002

(87) PCT Pub. No.: WO01/89375

PCT Pub. Date: Nov. 29, 2001

(65) Prior Publication Data

US 2003/0123028 A1 Jul. 3, 2003

(30) Foreign Application Priority Data

May 19, 2000 (AU) .................................... PQ7625

(51) Int. Cl.
*A61B 3/10* (2006.01)
(52) U.S. Cl. .................................... 351/214
(58) Field of Classification Search ................ 351/200, 351/211–221, 206, 245, 246; 607/88; 250/363.08
See application file for complete search history.

(56) References Cited

U.S. PATENT DOCUMENTS

| 4,357,079 A | * | 11/1982 | Karasawa ..................... 351/211 |
| 5,712,482 A | * | 1/1998 | Gaiser et al. .......... 250/363.08 |
| 5,822,036 A | * | 10/1998 | Massie et al. ............... 351/219 |
| 6,003,991 A | | 12/1999 | Viirre |
| 6,050,688 A | | 4/2000 | Grinblat |
| 6,286,958 B1 | | 9/2001 | Koest et al. |
| 6,319,273 B1 | * | 11/2001 | Chen et al. .................... 607/88 |

FOREIGN PATENT DOCUMENTS

| DE | 29913602 | 11/1999 |
| GB | 2 167 919 | 6/1986 |
| WO | 96/17545 | 6/1996 |
| WO | 97/14350 | 4/1997 |
| WO | 97/36537 | 10/1997 |
| WO | 99/33393 | 7/1999 |

* cited by examiner

*Primary Examiner*—George Manuel
(74) *Attorney, Agent, or Firm*—Frommer Lawrence & Haug LLP; Thomas J. Kowalski; Anne-Marie C. Yvon

(57) ABSTRACT

A portable slit-lamp apparatus, including a body (11) able to be held in the hand of an operator and a solid state lamp means (55) and associated optics (52) carried by the body for generating a narrow beam of light and projecting the beam onto the cornea of a patient s eye for reflection by structures of the eye, when the body is held at a suitable position in front of the eye. Means (22) is mounted in cooperation with the body and the solid state lamp means to detect a reflection of the narrow beam of light by structures of the eye and to make an image thereof, which image is, or is processable to provide, a digital record of the reflection.

37 Claims, 2 Drawing Sheets

PORTABLE SLIT LAMP

FIELD OF THE INVENTION

This invention relates generally in one aspect to slit-lamps for use in ophthalmic diagnosis. In another aspect, the invention is concerned with the application of a slit-lamp to remote ophthalmic diagnosis.

BACKGROUND OF THE INVENTION

The cornea of the eye is essential for good vision. It is the outermost tissue of the eye and functions like a window controlling the entry of light into the eye. An established branch of ophthalmic medicine is the examination of optically reflected corneal images as a diagnostic tool in the identification of trachomatous scarring, cataracts, injuries or bacterial and viral infections. These images are captured using slit-lamps to provide a narrow beam of light of elongated slit-shaped cross-section which is projected onto the cornea to study the surface characteristics. The reflected image is in effect an optical section of the anterior part of the eye including the cornea, the anterior chamber, the iris or the lens and the anterior part of the vitreous. For identifying some conditions, the ophthalmologist seeks to identify changes in the reflected image over time.

Commercial slit-lamp instruments are generally available in relatively expensive fixed installations in clinics and ophthalmologists' rooms. Patients must generally come to the instruments and this presents a problem in monitoring the eye health of populations in more sparsely populated and remote regions.

It is an object of this invention to provide a portable slit-lamp which assists in addressing these disadvantages with the form and siting of conventional slit-lamp instruments.

At least one portable slit-lamp is commercially available but this instrument is only a partial solution to the problem discussed above in that it does at least allow the ophthalmologist or ophthalmic surgeon to come to the patient.

SUMMARY OF THE INVENTION

In a first aspect, the invention provides portable slit-lamp apparatus, including a body able to be held in the hand of an operator. Solid state lamp means and associated optics are carried by the body for generating a, narrow beam of light and projecting the beam onto the cornea of a patient's eye for reflection by structures of the eye, when the body is held at a suitable position in front of the eye. Means is mounted in cooperation with the body and the solid state lamp means to detect a reflection of the narrow beam of light by structures of the eye and to make an image thereof, which image is, or is processable to provide, a digital record of the reflection.

The narrow beam is preferable of elongated slit-shaped cross-section.

The solid state lamp means is conveniently one or more light emitting diodes.

Advantageously, the solid state lamp means consists of a pair of solid state lamps whereby the lamp means is generally elongated.

The associated optics preferably includes an elongated lens of uniform cross-section, eg. a semi-cylindrical lens, arranged with its axis generally aligned with said elongated lamp means, for focussing a light beam emitted thereby of elongated cross-section towards said cornea, as said narrow beam of light.

Preferably, the associated optics include structure defining a slit aligned with and disposed to receive light from said elongated light means, to define a light beam of elongated cross-section.

Preferably, there are a pair of said solid state lamp means and associated optics selectively operable for generating and projecting respective said narrow beams of light onto the corneas of the patients left and right eyes respectively.

The means to detect the reflection and to make a digital record of the reflection of the narrow beam of light may be a CCD camera but is preferably a digital camera and associated optics.

The portable slit-lamp apparatus preferably further includes means to transmit the digital record for storage, and for review and diagnosis subsequently and/or at a remote location. Such means to transmit the digital record may comprise a cabling link to a local computer for storage and, in one or more embodiments, for online transmission to the remote location.

Alternatively, the portable slit-lamp may include a radio, microwave or infrared transmitter for communicating with the local computer.

Preferably, the portable slit-lamp apparatus further includes means mounted to the body for providing background illumination of the cornea. This illumination is preferably of adjustable brightness.

Means is preferably provided to adjust the width of the narrow beam of, light.

In a second aspect, the invention provides a method of ophthalmic diagnosis utilising a portable slit lamp apparatus according to the first aspect of the invention including:

at a first location, projecting a narrow beam of light, generated by said solid state lamp means and associated optics, onto the cornea of a patient's eye;

detecting, with said detecting means, a reflection of said beam of light by structures of the eye;

making a digital record of the reflection; and transmitting said digital record to a second location remote from the first for review and diagnosis.

Preferably, said narrow beam is of elongated slit-shaped cross-section.

Preferably, the method further includes reviewing the digital record of the reflection and performing an ophthalmic diagnosis on the basis of the record. Advantageously, the digital record is reproduced as a viewable image.

The transmission of the digital record of the reflection may be by transport of a memory device, eg. a computer memory disk, but is preferably online, eg. via the internet or other network means from a local computer at the first location.

BRIEF DESCRIPTION OF THE DRAWINGS

The invention will now be further described by way of example only, with reference to the accompanying drawings, in which.

EMBODIMENTS OF THE INVENTION

Figure 1:
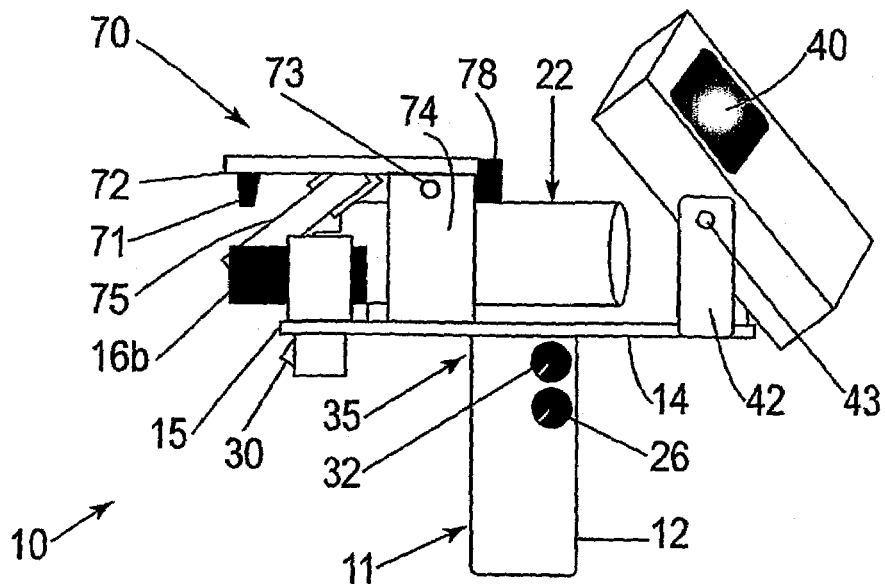
FIG. 1 is a diagrammatic side elevation, with a portion depicted 3-dimensionally, of portable slit-lamp apparatus according to an embodiment of the invention.

The illustrated portable slit-lamp apparatus 10 includes a portable body 11 made up of a generally cylindrical handle 12 and, atop the handle, a mounting plate 14. Handle 12 is of such a diameter that it is able to be readily and comfortably held in an adult hand by grasping the hand about the handle. Handle 12 is a housing for the electrical circuitry of the device and also optionally carries a power supply such as a battery pack.

Plate 14 supports, on its upper surface adjacent its front edge 15, a pair of slit-lamp devices 16a, 16b. Each device 16a, 16b contains a pair of adjacent solid state lamps 50, 51 (FIG. 3) as light source 55 and associated optics 52 for generating a narrow beam of light of elongated slit-shaped cross-section, and projecting the beam respectively onto the corneas of a patient's left and right eyes, when the apparatus is held (by grasping handle 12) at a suitable position in front of the respective eye.

Further supported atop plate 14, generally at the centre front of the plate, is preferably a digital camera but may be an analogue camera such as a CCD lipstick camera 22. Camera 22 includes optics whereby the reflection of the aforementioned narrow beam of light by structures of the eye is detected by the camera and a digital record of the reflection thereby obtained. The normal practice is to direct the beam towards the respective eye off the central optical axis, eg. about 20° and typically greater than 5°, in order to avoid red reflex images from the back of the eye.

Slit-lamp devices may be at a fixed angle as illustrated, or mounted for pivotal adjustment to different angles. Magnification may also be variable.

The camera image is viewed in real time on a rear-facing LCD screen 40 mounted between upstanding brackets 42 on mounting plate 14. Screen 40 is pivotally mounted at 43 to brackets 42 to allow adjustment of its angular orientation. When it is desired to capture and store an image, the operator triggers image capture button 35 on handle 12, and the captured image is transmitted as a digital record to a local personal computer (PC) 25 via a cabling link 24. When the operator of the lamp apparatus presses button 35, an enable signal is sent to the computer via cabling 24 and the serial (or COM) port 26 of the PC, to trigger customised applications of the software to detect the signals and grab images using a frame grabber in the PC. Thus a particular image or video clip can be selected for saving on file in the PC. In an alternative wireless embodiment, the instrument may be provided with an infra-red or radio transmitter for communicating with the PC to transfer images. In another alternative, with a digital camera the camera may store digital image records on a memory card that can be downloaded to the PC.

The arrangement of the camera 22 is such that the image captured by the camera is substantially the exact slit image seen directly from the slit-lamp.

Figure 3:
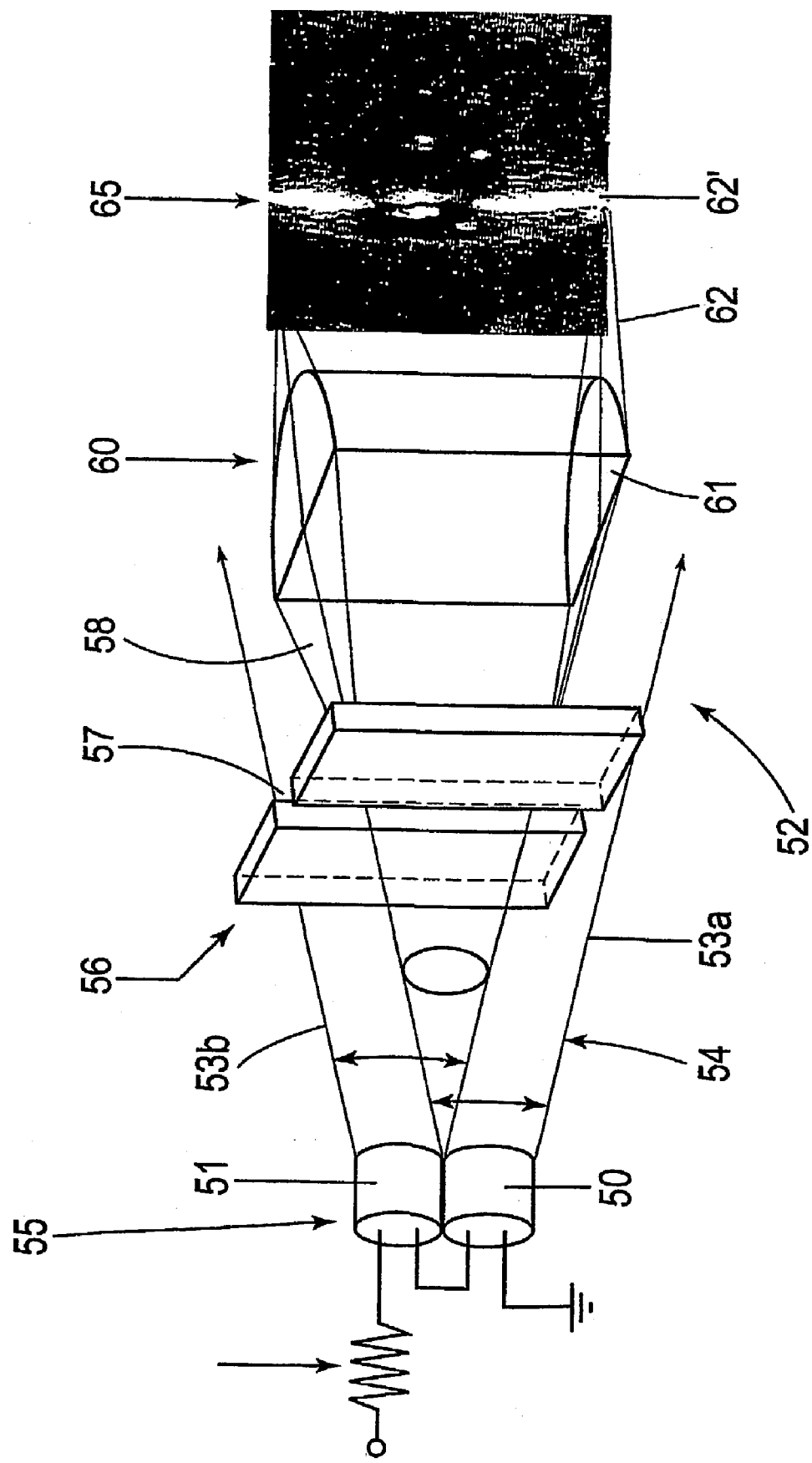
FIG. 3 is an optical ray diagram of the respective arrangements in the apparatus of FIG. 1 for generating and projecting a narrow beam or slit of light onto the cornea of a patient's eye. A typical slit lamp image is also included in FIG. 3.

As mentioned, the light source 55 of each slit-lamp device 16 is a pair of adjacent solid state lamps. Suitable such lamps are light emitting diodes (LED) 50, 51 (FIG. 3). Use of diodes rather than a small bulb permits a much longer life between replacements of the battery contained within handle 12. A switch 26 is provided at the side of handle 12 for altering output of the diodes and therefore the brightness of the projected narrow beam of light to suit the patient's cornea, for example according to whether the iris is blue or brown or otherwise darker.

The optics 52 associated with the LEDs 50, 51 of each slit lamp device 16 are depicted in the optical ray diagram of FIG. 3. The pair of adjacent diodes 50, 51 forms an elongated light source that generates an initial beam 54 formed by the overlapping cones (typically 20°) of light 53a, 53b emitted by the diodes. Diodes 50, 51 are preferably white LEDs. Beam 54 is laterally trimmed by structure 56 defining a narrow slit 57 which is optionally adjustable but typically of width about 0.1 mm. The beam 58 emerging from slit 57 is focussed by a piano-convex lens in the form of a semi-cylindrical prism lens 60, ie. a prism lens of uniform semi-circular cross-section, so as to be aligned with slit 57 and with the elongated light source. The planar face 61 of prism lens 60 faces the slit and is orthogonal to the beam. Lens 60 focuses beam 58 towards the cornea of the respective eye to form the narrow beam of light 62 projected onto the cornea. Lens 60 also longitudinally trims beam 58 back to a segment formed by the overlapping of the light cones from the LEDs 50, 51.

Figure 2:
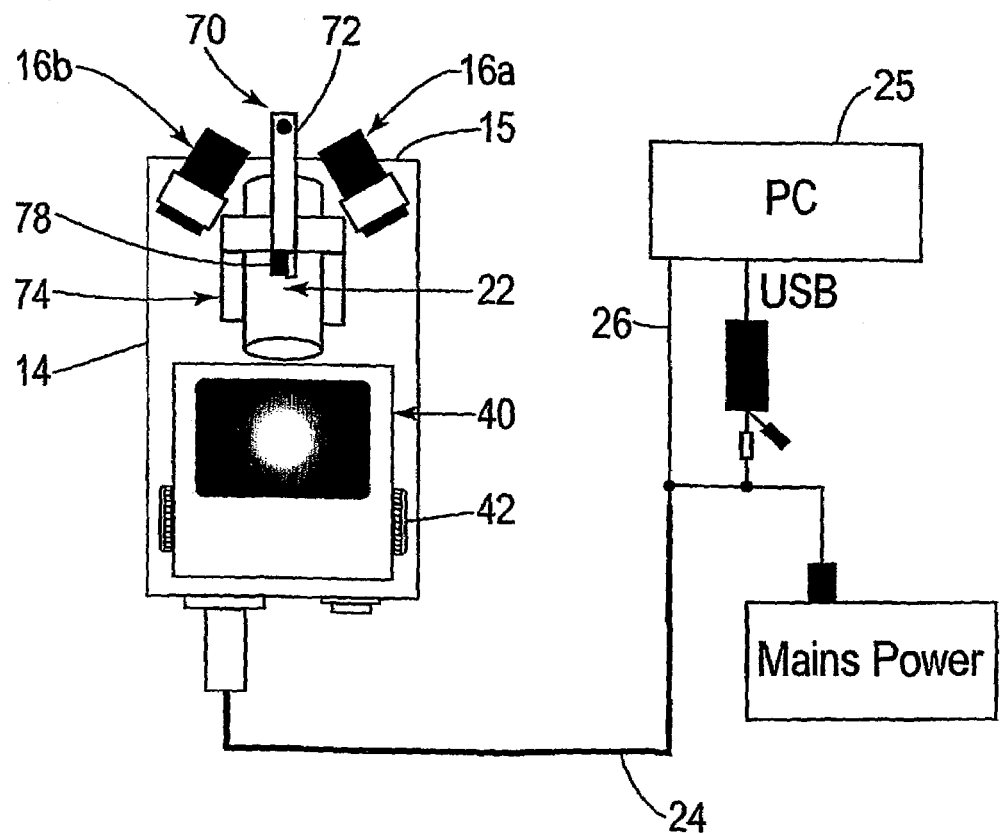
FIG. 2 is a plan view of the apparatus of FIG. 1, also depicting a cabling link to a local computer.

FIG. 2 also includes a typical slit lamp image 65 captured by camera 22. The image of the reflection of narrow light beam 62 is readily apparent at 62'.

The apparatus includes a switch (not shown), typically on handle 12, for selectively operating one or other of slit lamp devices 16a, 16b according to whether a left-eye or right-eye image is required.

Projecting forwardly from a mount under plate 14 just behind its front edge 15 is an additional diode light source 30 to provide background illumination of the cornea. A second control switch 32 at the side of handle 12 permits adjustment of the brightness of the background illumination to suit ambient conditions.

As mentioned, the slit 57 of each slit-lamp device 16a, 16b is adjustable so that the width of the slit of light can be varied. For example, when the slit is narrower, an optical section of the anterior part of the eye is seen: from the exterior inwards this consists of a cornea, a dark interval corresponding to the anterior chamber, and either the iris or the lens and the anterior part of the vitreous. When the slit is a little wider, blocks of the transparent tissues are illuminated. It will be understood that light that is brought to focus in a vertical line, ie. a slit, is directed into the eye so that the beam of light cuts a slice through the transparent and semi-transparent structures. In this way, an optical section is cut through the tissue. It is easy to see the shape and thickness of transparent structures and to localise the position or depth of any alterations in these structures.

To further enhance its flexibility, apparatus 10 is fitted with a red reflex unit 70 comprising a white diode 71 on a projecting arm 72 which is pivotally mounted at 73 above camera 22 on an inverted U sub-frame 74. When unit 70 is in the position shown in FIG. 1, the beam from diode 71 is reflected to the eye, on the optical axis of camera 22 and the central optical axis of the eye, by an oblique beamsplitter 75 (on arm 72) that also transmits red reflex images reflected off the back of the eye to camera 22. In this condition the apparatus can be employed for detection of lens opacities (eg. cataract) and abnormalities (eg. subluxation).

The red reflex unit 70 is rendered inoperable by pivoting arm 72 upwardly about mountings 73 to remove the beamsplitter 75 from the optical axis of the camera 22. A switch device 78 at the back of unit 70 switches diode 71 and the diodes of slit-lamp devices 16a, 16b on and off or off and on according to the position of the unit.

In a further modification, with the red reflex unit in the position shown in FIG. 1, a suitable lens arrangement placed between beamsplitter 75 and the eye makes it possible to obtain, with camera 22 and using lamp 71, an image of the retina, ie. an image normally only able to be obtained with a separate instrument such as an ophthalmoscope or fundus camera.

It will be appreciated that the illustrated instrument has the great practical advantage that it can be carried to remote locations and employed, perhaps by semi-skilled or non-specialist personnel, to capture and store slit-lamp images in digital format in a computer hard disk or other storage device for transfer to another location for subsequent diagnosis by ophthalmologists or other skilled professionals. In accordance with a preferred aspect of the invention, however, the digital record of the images may be transmitted online, eg via the internet or other network means, to the other location for review and diagnosis. The diagnosis may then be transmitted or forwarded back, eg. as an online response to the forwarder of the image.

The invention claimed is:

1. Portable slit-lamp apparatus, including:
   a body;
   solid state lamp means and associated optics carried by said body for generating a narrow beam of light and projecting the beam onto the cornea of a patient's eye for reflection by structures of the eye, when the body is held at a suitable position in front of the eye; and
   means mounted in cooperation with said body and said solid state lamp means to detect a reflection of said narrow beam of light by structures of the eye and to make an image thereof, which image is, or is processable to provide, a digital record of said reflection;
   wherein the apparatus is able to be held in the hand of an operator; and
   wherein said associated optics include an elongated lens of uniform cross-section arranged with its axis generally aligned with said elongated lamp means, for focusing a light beam emitted thereby of elongated cross-section towards said cornea, as said narrow beam of light.

2. Apparatus according to claim 1 wherein said solid-state lamp means comprises one or more light emitting diodes.

3. Apparatus according to claim 2 wherein said means to detect the reflection of said narrow beam of light is a digital camera and associated optics.

4. Apparatus according to claim 2 wherein said means to detect the reflection of said narrow beam of light is a CCD camera and associated optics.

5. Apparatus according to claim 2, further including means to transmit said digital record for storage, and for review and diagnosis subsequently and/or at a remote location.

6. Apparatus according to claim 1 wherein said narrow beam is of elongated slit-shaped cross section.

7. Apparatus according to claim 6 wherein said solid-state lamp means consists of a pair of solid-state lamps whereby the lamp means is generally elongated.

8. Apparatus according to claim 7 wherein said solid-state lamps are light emitting diodes.

9. Apparatus according to claim 8 wherein said associated optics include structure defining a slit aligned with and disposed to receive light from said elongated light means, to define a light beam of elongated cross section.

10. Apparatus according to claim 9, wherein said lens is a semi-cylindrical lens.

11. Apparatus according to claim 7 wherein said means to detect the reflection of said narrow beam of light is a digital camera and associated optics.

12. Apparatus according to claim 7 wherein said means to detect the reflection of said narrow beam of light is a CCD camera and associated optics.

13. Apparatus according to claim 7, further including means to adjust the width of said narrow beam of light.

14. Apparatus according to claim 7, further including means to transmit said digital record for storage, and for review and diagnosis subsequently and/or at a remote location.

15. Apparatus according to claim 1, wherein said lens is a semi-cylindrical lens.

16. Apparatus according to claim 1 wherein there are a pair of said-solid state lamp means and associated optics selectively operable for generating respective said narrow beams of light and projecting them onto the corneas of the patients left and right eyes respectively.

17. Apparatus according to claim 1 wherein said means to detect the reflection of said narrow beam of light is a digital camera and associated optics.

18. Apparatus according to claim 17, further including means to transmit said digital record for storage, and for review and diagnosis subsequently and/or at a remote location.

19. Apparatus according to claim 1 wherein said means to detect the reflection of said narrow beam of light is a CCD camera and associated optics.

20. Apparatus according to claim 19, further including means to transmit said digital record for storage, and for review and diagnosis subsequently and/or at a remote location.

21. Apparatus according to claim 1, further including means mounted to said body for providing background illumination of the cornea.

22. Apparatus according to claim 21 further including means to adjust the brightness of said background illumination.

23. Apparatus according to claim 1, further including means for adjusting the brightness of said solid-state lamp means.

24. Apparatus according to claim 1, further including means to adjust the width of said narrow beam of light.

25. Apparatus according to claim 1, further including means to selectively project a beam of light from a solid-state lamp to obtain red reflex.

26. Apparatus according to claim 1, further including solid-state lamp and lens means to selectively project a beam of light to obtain an image of the retina.

27. Apparatus according to claim 1, further including means to transmit said digital record for storage, and for review and diagnosis subsequently and/or at a remote location.

28. Apparatus according to claim 27, wherein said means to transmit the digital record comprises a cabling link to a local computer for storage or optionally for online transmission to the remote location.

29. Apparatus according to claim 27, wherein said means to transmit the digital record comprises a radio, microwave or infra-red transmitter for communicating with a local computer for storage or optionally for online transmission to the remote location.

30. A method of ophthalmic diagnosis utilizing a portable slit lamp apparatus comprising
   i) a body able to be held in the hand of an operator;

ii) solid state lamp means and associated optics carried by said body for generating a narrow beam of light and projecting the beam onto the cornea of a patient's eye for reflection by structures of the eye, when the body is held at a suitable position in front of the eye, wherein said associated optics include an elongated lens of uniform cross-section arranged with its axis generally aligned with said elongated lamp means, for focusing a light beam emitted thereby of elongated cross-section towards said cornea, as said narrow beam of light; and iii) means mounted in cooperation with said body and said solid state lamp means to detect a reflection of said narrow beam of light by structures of the eye and to make an image thereof, which image is a digital record of said reflection the method comprising:

at first location, projecting a narrow beam of light, generated by said solid-state lamp means and associated optics, onto the cornea of a patient's eye;

detecting, with said detecting means, a reflection of said beam of light by structures of the eye;

making a digital record of the reflection; and transmitting or forwarding said digital record to a second location remote from the first for review and diagnosis.

31. A method according to claim 30 wherein said narrow beam is of elongated slit-shaped cross section.

32. A method according to claim 30 further including reviewing the digital record of the reflection and performing an ophthalmic diagnosis on the basis of the record.

33. A method according to claim 32 further including transmitting or forwarding the diagnosis to the first location.

34. A method according to claim 30 further including reproducing said digital record as a viewable image.

35. A method according to claim 30 further including reviewing the digital record of the reflection and performing an ophthalmic diagnosis on the basis of the record.

36. A method according to claim 35 further including transmitting or forwarding the diagnosis to the first location.

37. A method according to claim 30 where said transmission of the digital record of the reflection and/or of the diagnosis is online via the internet or other network means from a local computer at the first location.

* * * * *